(12) United States Patent
Underwood

(10) Patent No.: US 7,671,015 B2
(45) Date of Patent: Mar. 2, 2010

(54) AEQUORIN-CONTAINING COMPOSITIONS AND METHODS OF USING SAME

(75) Inventor: Mark Y. Underwood, Madison, WI (US)

(73) Assignee: Quincy Bioscience, LLC, Madison, WI (US)

( * ) Notice: Subject to any disclaimer, the term of this patent is extended or adjusted under 35 U.S.C. 154(b) by 492 days.

(21) Appl. No.: 11/571,043

(22) PCT Filed: Jun. 21, 2005

(86) PCT No.: PCT/US2005/021770

§ 371 (c)(1), (2), (4) Date: Dec. 20, 2006

(87) PCT Pub. No.: WO2006/010004

PCT Pub. Date: Jan. 26, 2006

(65) Prior Publication Data

US 2008/0287350 A1    Nov. 20, 2008

Related U.S. Application Data

(63) Continuation of application No. 10/872,795, filed on Jun. 21, 2004, now abandoned.

(51) Int. Cl.
- *A01N 37/18* (2006.01)
- *A61K 49/00* (2006.01)
- *C07K 14/00* (2006.01)

(52) U.S. Cl. ............ 514/2; 424/9.1; 530/350
(58) Field of Classification Search ............ None
See application file for complete search history.

(56) References Cited

U.S. PATENT DOCUMENTS 6,800,492 B2    10/2004    Baubet et al.

OTHER PUBLICATIONS

Leclerc et al. Mechanisms of Development, 64:105-110, 1997.*
Ozduman et al., Pediatr Neurol, 30(3):151-162, 2004.*
Perrot et al., Am J Respir Crit Care Med, 167(4):490-511, Feb. 2003.*
Allen et al., J Physiol, 410:297-323, 1989.*
Kihara et al., Circulation Res, 65(4):1029-1044, 1989.*
Baubet et al.; Chimeric green fluorescent protein-aequorin as bioluminescent Ca2+ reporters at the single-cell level, Proc. Natl. Acad. Sci. Jun. 2000, vol. 97 No. 13, pp. 7260-7265.
Mithofer et al.; Aequorin-based measurements of intracellular Ca2+ signatures in plant cells; Biological Procedures; Dec. 2002, vol. 4 No. 1, pp. 105-118.
Jiang et al.; Recycling application of aequorin introduction solution in the measurement of platelet cytoplasm free calcium; Chinese Journal of Hematology, 1991, vol. 12, No. 2.
PCT Search Report WO 2006/010004 A3.

* cited by examiner

*Primary Examiner*—John D. Ulm
*Assistant Examiner*—Stacey MacFarlane
(74) *Attorney, Agent, or Firm*—Quarles & Brady LLP

(57) ABSTRACT

Compositions containing aequorin and methods for their use in preventing and/or alleviating symptoms and disorders related to calcium imbalance are provided by the present invention.

1 Claim, 2 Drawing Sheets

AEQUORIN-CONTAINING COMPOSITIONS AND METHODS OF USING SAME

CROSS REFERENCE TO RELATED APPLICATION

This application represents the U.S. National Stage Filing under 35 U.S.C. § 371 of International Application No. PCT/US2005/021770, filed Jun. 21, 2005, which was published in English, designated/elected the United States of America, and claimed priority to U.S. patent application Ser. No. 10/872, 795, filed Jun. 21, 2004, both of which are incorporated by reference into the present application in their entirety for all purposes.

FIELD OF THE INVENTION

This invention relates generally to compositions useful for the maintenance of calcium homeostasis. In particular, this invention is directed to aequorin-containing pharmaceutical and nutraceutical compositions useful in preventing and/or alleviating diseases or symptoms associated with calcium imbalance.

BACKGROUND OF THE INVENTION

Calcium is the fifth most abundant element in the human body and occurs mainly in the bone. More than 99% of the calcium in the body is stored in the skeleton, which constantly exchanges its supply with the remaining 1% dissolved in body fluids and soft tissue, such as the blood. The control of this exchange is largely dictated by the endocrine system which senses the concentration of ionized calcium in the plasma and directs calcium exchange to maintain this critical balance. Only a small fraction of the 1% of calcium in interstitial fluids and the soft tissues is ionized and soluble, the rest being bound to proteins, particularly calcium-binding proteins (CaBPs). These CaBPs are known to function in the maintenance of calcium homeostasis. As the body requires specific concentrations of calcium ion in order to carry out requisite physiological processes, the maintenance of calcium homeostasis is therefore of critical importance for bodily health. Proper ionic calcium concentrations in plasma and body fluids are understood by the medical community to be critical in bodily functions, including, but not limited to neuronal excitability, muscle contraction, membrane permeability, cell division, hormone secretion and bone mineralization. A disruption in calcium homeostasis, i.e., a calcium imbalance, is associated with many diseases, syndromes and conditions, including, but not limited to, cancer, heart disease and neurodegenerative disease.

In the past, calcium channel antagonists, which block the flow of calcium between cell interiors and interstitial fluid, have been widely-prescribed as pharmaceutical agents useful in the prevention of calcium-related disorders including hypertension, angina, asthma, migraines and neural deterioration. For example, nimidopine has been found to improve clinical symptomatology and cognitive functions in dementia by alleviating a calcium imbalance which causes neural deterioration. However, many of these calcium channel antagonists have unwanted side effects including, but not limited to, malaise, fluid retention, heartburn, erratic heart rate, dizziness, upset stomach and, in rare cases, fainting, fever and excessive bleeding.

A need therefore exists for new and alternative therapeutics which alleviate or prevent calcium imbalance. In particular, pharmaceutical or nutraceutical compositions which have reduced side effects as compared to prior agents are desired and, if discovered, would meet a long felt need in the medical and nutritional health communities.

SUMMARY OF THE INVENTION

The present invention provides pharmaceutical and nutraceutical compositions which are advantageous in the alleviation and/or prevention of symptoms or disorders associated with calcium imbalance. Such compositions include aequorin in combination with acceptable carriers for administration to a subject by a variety of routes. Accordingly, the present invention is directed to pharmaceutical compositions comprising effective amounts of aequorin in combination with an acceptable carrier, hi other embodiments, the present invention is directed to nutraceutical compositions including effective amounts of aequorin in combination with an acceptable carrier. In certain embodiments, nutraceutical compositions include, in addition to aequorin, at least one other component recognized as providing nutraceutical benefit.

In another embodiment, the invention further provides methods for treating a symptom or disorder associated with calcium imbalance by administering to a patient in need of such treatment a therapeutically-effective amount of aequorin.

In yet another embodiment, the invention encompasses the use of aequorin for the manufacture of compositions useful in the alleviation or prevention of symptoms or disorders associated with calcium imbalance.

Other objects, features and advantages of the present invention will become apparent after review of the specification and claims.

DETAILED DESCRIPTION OF THE INVENTION

I. In General

Figure 1:
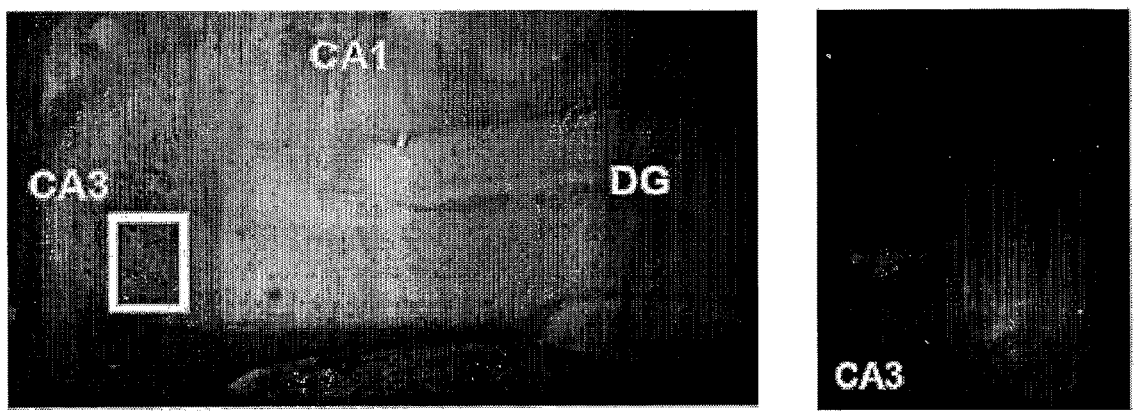
FIG. 1 depicts fluorescence micrograph depicting the uptake of aequorin by hippocampal neurons.

Before the present methods are described, it is understood that this invention is not limited to the particular methodology and materials described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals and methodologies which are reported in the publications which might be used in connection with the invention. Nothing herein is to be construed as an admission that the invention is not entitled to antedate such disclosure by virtue of prior invention.

II. The Invention

Aequorin is aphotoprotein originally isolated from luminescent jellyfish and other marine organisms. The aequorin complex comprises a 22,000-dalton apoaequorin protein, molecular oxygen and the luminophore coelenterazine. When three Ca2+ ions bind to this complex, coelenterazine is oxidized to coelenteramide, with a concomitant release of carbon dioxide and blue light. Aequorin is not exported or secreted by cells, nor is it compartmentalized or sequestered within cells. Accordingly, aequorin measurements have been used to detect Ca2+ changes that occur over relatively long periods. In several experimental systems, aequorin's luminescence was detectable many hours to days after cell loading. It is further known that aequorin also does not disrupt cell functions or embryo development.

Because of its Ca2+-dependent luminescence, the aequorin complex has been extensively used as an intracellular Ca2+ indicator. *Aequorea Victoria* aequorin has been specifically used to: (1) analyze the secretion response of single adrenal chromaffin cells to nicotinic cholinergic agonists; (2) clarify the role of Ca2+ release in heart muscle damage; (3) demonstrate the massive release of Ca2+ during fertilization; (4) study the regulation of the sarcoplasmic reticulum Ca2+ pump expression in developing chick myoblasts; and (5) calibrate micropipets with injection volumes of as little as 3 picoliters.

Conventional purification of aequorin from the jellyfish *Aequorea Victoria* requires laborious extraction procedures and sometimes yields preparations that are substantially heterogeneous or that are toxic to the organisms under study. Two tons of jellyfish typically yield –125 mg of the purified photoprotein. In contrast, recombinant aequorin is preferably produced by purifying apoaequorin from genetically engineered *Escherichia coli*, followed by reconstitution of the aequorin complex in vitro with pure coelenterazine. This method of preparation yields a pure, nontoxic, fully charged aequorin complex that is suitable for use in the present invention. An exemplary commercial preparation of aequorin useful in the present invention is available from Molecular Probes, Inc., under the trade name AQUALITE. Aequorin useful in the present invention has therefore been described and is commercially-obtainable through purification schemes and/or syntheses known to those of skill in the art.

The function of aequorin is distinguished by several characteristics: aequorin is non-toxic and does not interfere with internal cellular stoichiometry. (Miller et al., *Methods Cell Biol.* 40:305-338 (1994)); the protein is non-toxic when introduced into foreign cells (Blinks, J. *Environ Health Persp* 83:75-81 (1990)). Each molecule of aequorin is known to bind up to three calcium ions (Inouye et al., *Proc. Natl. Acad. Sci. U.S.A.*, 82:3154-3158 (1985)).

The present invention is directed to the administration of aequorin-containing compositions to a subject in order to correct or maintain the calcium balance in that subject. The maintenance of ionic calcium concentrations in plasma and body fluids is understood to be critical to a wide variety of bodily functions, including, but not limited to neuronal excitability, muscle contraction, membrane permeability, cell division, hormone secretion and bone mineralization. Disruption in calcium homeostasis, i.e., a calcium imbalance, is understood to cause and/or correlate with many diseases, syndromes and conditions. The study of CaBPs has led to their recognition as protective factors acting in the maintenance of proper ionic calcium levels.

In certain embodiments, the methods of the present invention comprise administering aequorin as the sole active ingredient for treating calcium imbalance, for delaying the progression of calcium imbalance, for preventing the onset of calcium imbalance, and for preventing and/or treating the recurrence of calcium imbalance. In other embodiments, the invention provides methods which comprise administering aequorin in combination with one or more additional agents having known therapeutic value.

As used herein, the term "treating" includes preventative as well as disorder remittent treatment. As used herein, the terms "reducing", "alleviating", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cell in contact with aequorin. As used herein, administration can be accomplished in vitro, i.e. in a test tube, or in vivo, i.e. in cells or tissues of living organisms, for example, humans. In preferred embodiments, the present invention encompasses administering the molecules useful in the present invention to a patient or subject. A "patient" or "subject", used equivalently herein, refers to a mammal, preferably a human, that either: (1) has a calcium imbalance-related disorder remediable or treatable by administration of aequorin; or (2) is susceptible to a calcium imbalance-related disorder that is preventable by administering aequorin.

As used herein, "pharmaceutical composition" means therapeutically effective amounts of aequorin together with suitable diluents, preservatives, solubilizers, emulsifiers, and adjuvants, collectively "pharmaceutically-acceptable carriers." As used herein, the terms "effective amount" and "therapeutically effective amount" refer to the quantity of active agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of a calcium imbalance-related disorder; and (b) the reversal or stabilization of a calcium imbalance-related disorder. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including parenteral, pulmonary, nasal and oral. In certain embodiments, the pharmaceutical composition is administered parenterally, paracancerally, transmucosally, transdermally, intramuscularly, intravenously, intradermally, subcutaneously, intraperitoneally, intraventricularly, intracranially or intratumorally.

Further, as used herein "pharmaceutically acceptable carriers" are well known to those skilled in the art and include, but are not limited to, 0.01-0.1 M and preferably 0.05 M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal, opthalmic, and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration, hi one embodiment, a pump may be used. In another embodiment, polymeric materials can be used. In yet another embodiment, a controlled release system can be placed in proximity to the therapeutic target, i.e., the prostate, thus requiring only a fraction of the systemic dose.

The pharmaceutical preparation can comprise aequorin alone, or can further include a pharmaceutically acceptable carrier, and can be in solid or liquid form such as tablets, powders, capsules, pellets, solutions, suspensions, elixirs, syrups, beverages, emulsions, gels, creams, ophthalmic formulations, or suppositories, including rectal and urethral suppositories. Pharmaceutically acceptable carriers also include gums, starches, sugars, cellulosic materials, and mixtures thereof. The pharmaceutical preparation containing aequorin can be administered to a patient by, for example, subcutaneous implantation of a pellet. In a further embodiment, a pellet provides for controlled release of aequorin over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating, or tablet-forming processes. For oral administration, aequorin or its physiologically-tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the anti-androgen compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared.

The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof. In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric, or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, aequorin or its physiologically-tolerated derivatives are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989)).

For use in medicine, the salts of aequorin may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of aequorin with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, aequorin-containing compositions described herein may be provided in the form of nutraceutical compositions where aequorin prevents the onset of or reduces or stabilizes various deleterious calcium imbalance-related disorders. The term "nutraceutical," or "nutraceutical composition", for the purposes of this specification, refers to a food item, or a part of a food item, that offers medical health benefits, including prevention and/or treatment of disease. A nutraceutical composition according to the present invention may contain only aequorin according to the present invention as an active ingredient or, alternatively, may further comprise, in admixture with dietary supplements including vitamins, co-enzymes, minerals, herbs, amino acids and the like which supplement the diet by increasing the total intake of that substance.

Therefore, the present invention provides methods of providing nutraceutical benefits to a patient comprising the step of administering to the patient a nutraceutical composition containing aequorin. Such compositions generally include an "nutraceutically-acceptable carrier" which, as referred to herein, is any carrier suitable for oral delivery including the aforementioned pharmaceutically-acceptable carriers suitable for the oral route. In certain embodiments, nutraceutical compositions according to the invention comprise dietary supplements which, defined on a functional basis, include immune boosting agents, anti-inflammatory agents, anti-oxidant agents, anti-viral agents, or mixtures thereof.

Immune boosters and/or anti-viral agents are useful for accelerating wound-healing and improved immune function; and they include extracts from the coneflowers, or herbs of the genus *Echinacea*, extracts from herbs of the genus *Sambuca*, and Goldenseal extracts. Herbs of the genus *Astragalus* are also effective immune boosters in either their natural or processed forms. *Astragalus* stimulates development into of stem cells in the marrow and lymph tissue active immune cells. Zinc and its bioactive salts, such as zinc gluconate and zinc acetate, also act as immune boosters in the treatment of the common cold.

Antioxidants include the natural, sulfur-containing amino acid allicin, which acts to increase the level of antioxidant enzymes in the blood. Herbs or herbal extracts, such as garlic, which contain allicin, are also effective antioxidants. The catechins, and the extracts of herbs such as green tea containing catechins, are also effective antioxidants. Extracts of the genus *Astragalus* also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body.

Bioflavonoids such as quercetin are also effective anti-inflammatory agents, and may be used as such in the inventive compositions. Anti-inflammatory herbal supplements and anti-inflammatory compounds derived from plants or herbs may also be used as anti-inflammatory agents in the inventive composition. These include bromolain, a proteolytic enzyme found in pineapple; teas and extracts of stinging nettle; turmeric, extracts of turmeric, or curcumin, a yellow pigment isolated from turmeric.

Another supplement which may be used in the present invention is ginger, derived from herbs of the genus *Zingiber*. This has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Supplements which assist in rebuilding soft tissue structures, particularly in rebuilding cartilage, are useful in compositions for treating the pain of arthritis and other joint disorders. Glucosamine, glucosamine sulfate, chondroitin, and chondroitin sulfate are particularly useful for this purpose. Chondroitin may be derived from a variety of sources, such as Elk Velvet Antler. Marine lipid complexes, omega 3 fatty acid complexes, and fish oil are also known to be useful in treating pain associated with arthritis.

Supplements useful in treating migraine headaches include feverfew and *Gingko biloba*. The main active ingredient in feverfew is the sesquiterpene lactone parthenolide, which inhibits the secretion of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists in treatment of migraines by stabilizing arteries and improving blood circulation.

Although some of the supplements listed above have been described as to their pharmacological effects, other supplements may also be utilized in the present invention and their effects are well documented in the scientific literature.

III. Examples

Example 1

Aequorin is Taken up by Hippocampal Neurons

Li a set of preliminary studies, aequorin was bilaterally injected directly into the hippocampus of 3 different adult rats. The rats were returned to their home cages for at least 24 hrs after which they were anesthetized and their brains removed, sectioned and stained for aequorin using a monoclonal anti-aequorin antibody. The primary antibody was then visualized using a secondary antibody conjugated to Alexa Fluor 594. FIG. 1 shows an example of aequorin-labeled hippocampal neurons using conventional fluorescence microscopy. The left panel is a photomicrograph of the hippocampus showing the location of the cannula tip in the CA1 region. The white rectangle indicates the location of the two aequorin labeled CA3 pyramidal neurons shown in the right panel. The data illustrate that direct infusion of aequorin into the hippocampus (left panel) results in labeling of pyramidal neurons in CA1 and CA3. Aequorin (6% w/v) was dissolved in calcium-free aCSF in the presence of 3% DMSO. The solution was slowly injected (rate ~1 µl/min) directly into the hippocampus using a syringe pump (volume ~1 µL per side). After completion of the injection, the delivery cannulae remained in place for about 1 min prior to removal. An example of two aequorin-containing CA3 pyramidal neurons is shown in the right panel (4OX objective). The data clearly demonstrate the delivery of aequorin directly into the brain and also that the aequorin spreads throughout the hippocampus and is then taken up by neurons in CA1, CA3, and the dentate gyrus.

Example 2

Effects of Aequorin on Cell Deathfollowing Ischemia

Figures 2, 3:
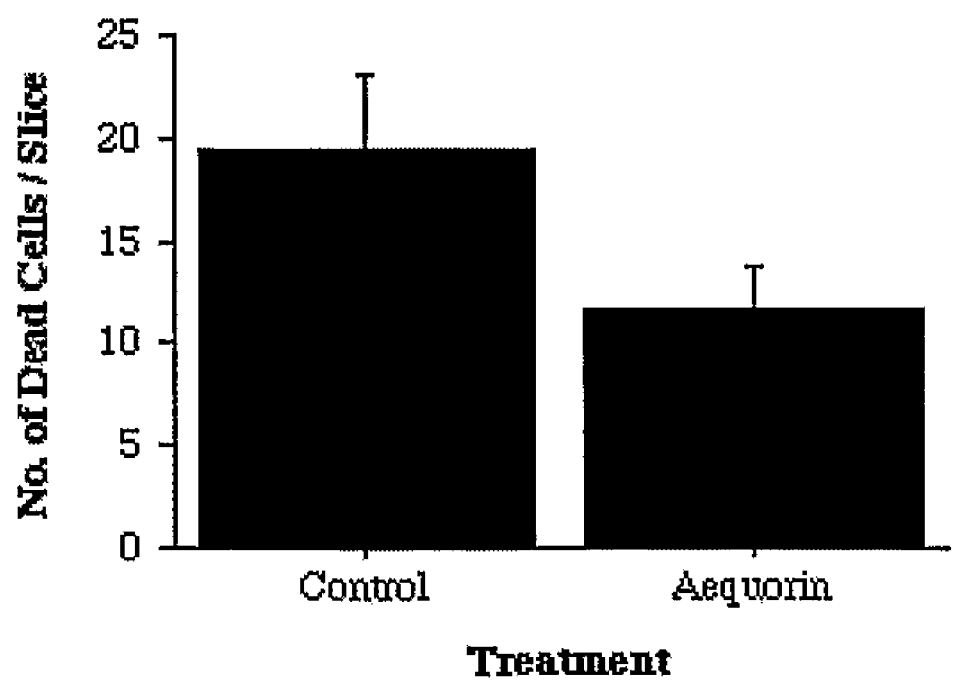
FIG. 2 shows video micrographs illustrating that aequorin is neuroprotective when administered prior to ischemia.
FIG. 3 illustrates a bar graph of the mean number of trypan blue containing (dead) neurons after ischemia.

An experiment was carried out to investigate the benefit of the calcium binding protein aequorin on ischemia. Aequorin (4%) was dissolved in calcium-free cerebrospinal fluid with 6% DMSO (dimethyl sulfoxide). Two to three hours later, a rat was anesthetized with isoflurane and sacrificed by decapitation. Four hundred micron thick brain slices were prepared using a temperature-controlled Vibratome. Slices were immediately placed into oxygenated (95% $O_2$/5% $CO_2$) artificial cerebrospinal fluid (aCSF) of the following composition (in niM): 124 NaCl, 2.8 KCl, 2 $MgSO_4$, 2 $NaH_2PO_4$, 2 $CaCl_2$, 26 $NaHCO_3$, 0.4 sodium ascorbate, 10 D-glucose, pH 7.4, ~30° C.). After a 1 hr recovery, slices were subjected to a 5 min ischemic episode. Ischemia was induced by replacing the glucose with fructose and replacing the oxygen with nitrogen. Following the 5 min ischemic challenge, slices were returned to normal oxygenated aCSF containing 0.04% trypan blue and incubated in the trypan blue aCSF for 30 min. The trypan blue exclusion method (healthy cells exclude trypan blue whereas dead or dying cells will take up the trypan blue and thus appear blue) is commonly used for evaluating cell death in cell culture or brain slices. After incubating in trypan blue, the sections were removed and placed in fixative overnight followed by 3 hr incubation in 30% sucrose. The 400 µm thick slices were then sectioned to a thickness of ~40 µm using a cryostat, mounted onto gelatin-coated slides and coverslipped. Referring to FIG. 2, it is apparent that there are more trypan blue stained (dead) neurons in the control (upper panel) relative to the aequorin (lower panel) injected neurons. FIG. 3 shows a bar graph of the mean number of trypan blue containing (dead) neurons after ischemia. This experiment demonstrates that injection of aequorin directly into the hippocampus confers neuroprotection against an ischemic insult.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating an ischemic insult to neurons in a subject's brain, comprising administering to the brain of a subject in need of such treatment an effective amount of aequorin, wherein the aequorin treats said ischemic insult to neurons in the subject's brain.

\* \* \* \* \*